(12) United States Patent
Carmichael et al.

(10) Patent No.: US 9,687,322 B2
(45) Date of Patent: Jun. 27, 2017

(54) DENTAL IMPLANT POSITIONING SYSTEM

(71) Applicants: Robert P. Carmichael, Toronto (CA); Warren Spitz, Toronto (CA)

(72) Inventors: Robert P. Carmichael, Toronto (CA); Warren Spitz, Toronto (CA)

(*) Notice: Subject to any disclaimer, the term of this patent is extended or adjusted under 35 U.S.C. 154(b) by 0 days.

(21) Appl. No.: 13/852,057

(22) Filed: Mar. 28, 2013

(65) Prior Publication Data
US 2014/0093838 A1  Apr. 3, 2014

Related U.S. Application Data

(60) Provisional application No. 61/707,121, filed on Sep. 28, 2012.

(51) Int. Cl.
A61C 19/04  (2006.01)
A61C 8/00  (2006.01)
A61C 1/08  (2006.01)

(52) U.S. Cl.
CPC ............ *A61C 8/0089* (2013.01); *A61C 1/084* (2013.01); *A61C 8/0024* (2013.01)

(58) Field of Classification Search
CPC ......... A61C 1/084; A61C 1/085; A61C 1/008; A61C 1/082; A61C 8/00–8/0098; A61B 6/14; A61B 17/17; A61B 17/176
USPC ................................ 433/72, 75, 76, 172–176
See application file for complete search history.

(56) References Cited

U.S. PATENT DOCUMENTS 5,362,234 A * 11/1994 Salazar ............... A61C 8/0024
433/169
5,989,025 A * 11/1999 Conley ................ A61B 17/176
408/241 B
7,008,227 B2 * 3/2006 Carmichael et al. ......... 433/174
2003/0165796 A1 * 9/2003 Carmichael .......... A61C 8/0024
433/174
2005/0149031 A1 * 7/2005 Ciccone ............ A61B 17/1615
606/280
2005/0164146 A1 * 7/2005 Cantor ......................... 433/173
2006/0093988 A1 * 5/2006 Swaelens et al. .............. 433/76
(Continued)

FOREIGN PATENT DOCUMENTS

JP  2011224147 A  11/2011

OTHER PUBLICATIONS

Extended European Search Report from corresponding European application 14774195.3 dated Nov. 11, 2016.
(Continued)

*Primary Examiner* — Yogesh Patel
(74) *Attorney, Agent, or Firm* — Gowling WLG (Canada) LLP

(57) ABSTRACT

A system is disclosed for installing a dental implant in a jawbone of a patient. The system includes a threaded drive shaft rotatable about an axis and a guide for supporting the drive shaft with its axis oriented in a path along which the implant is to be installed. The guide has a threaded bore for receiving a drive shaft and an opening which extends parallel to the axis of the drive shaft and opens radially outwardly from the bore. The drive shaft can then be engaged with and disengaged from the guide by radial displacement of the shaft parallel to its axis. A drill is adapted to be releasably coupled to a leading end portion of the drive shaft and may be a self-drilling implant. Rotating the drive shaft causes the drill to penetrate the jawbone of the patient.

7 Claims, 9 Drawing Sheets

(56) References Cited

U.S. PATENT DOCUMENTS

2010/0297574 A1* 11/2010 Llop et al. .................. 433/75
2012/0109140 A1*  5/2012 Akutsu ....................... 606/96

OTHER PUBLICATIONS

English Abstract of Japanese Patent Publication No. 2011224147 published Nov. 10, 2011.

* cited by examiner

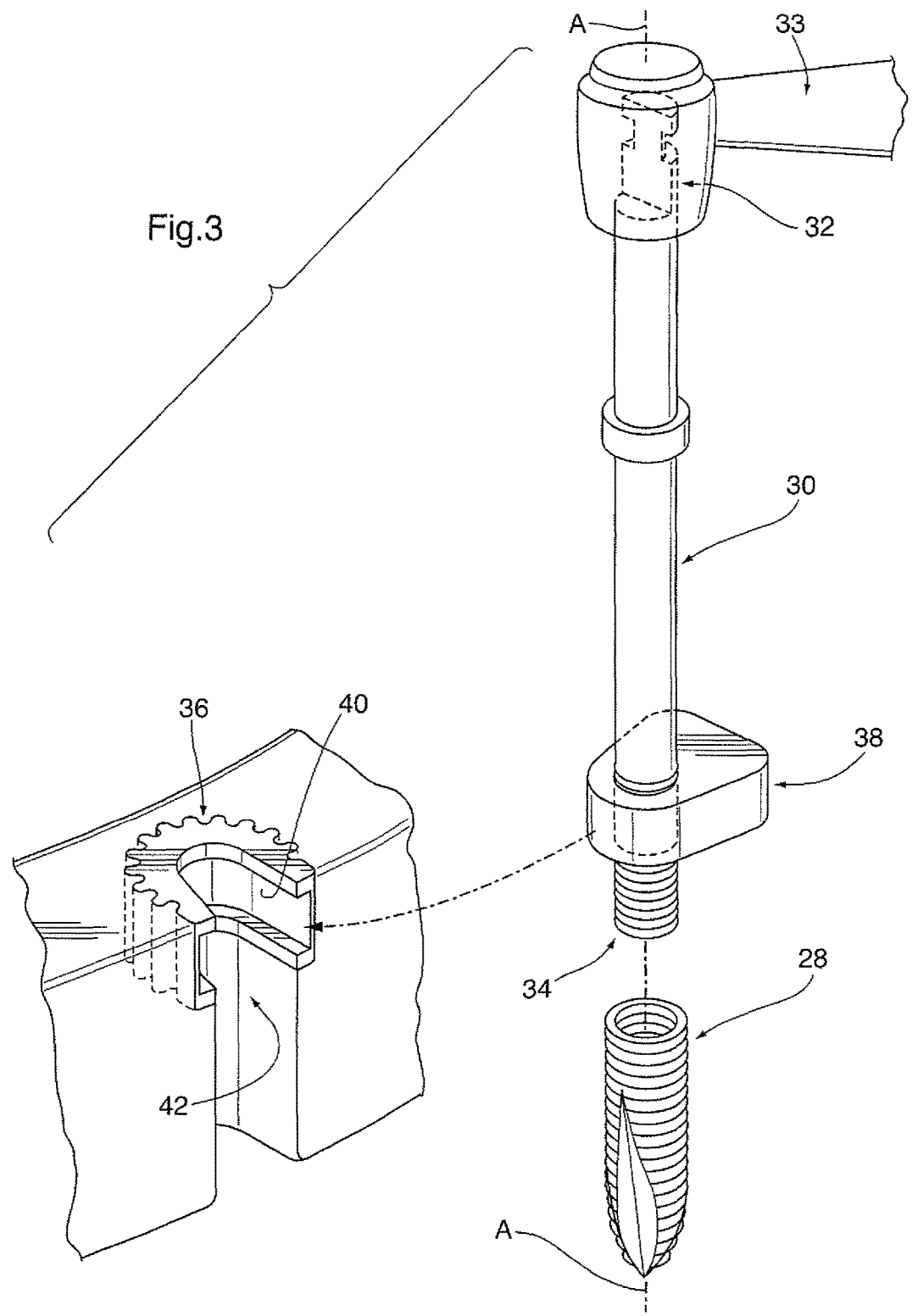

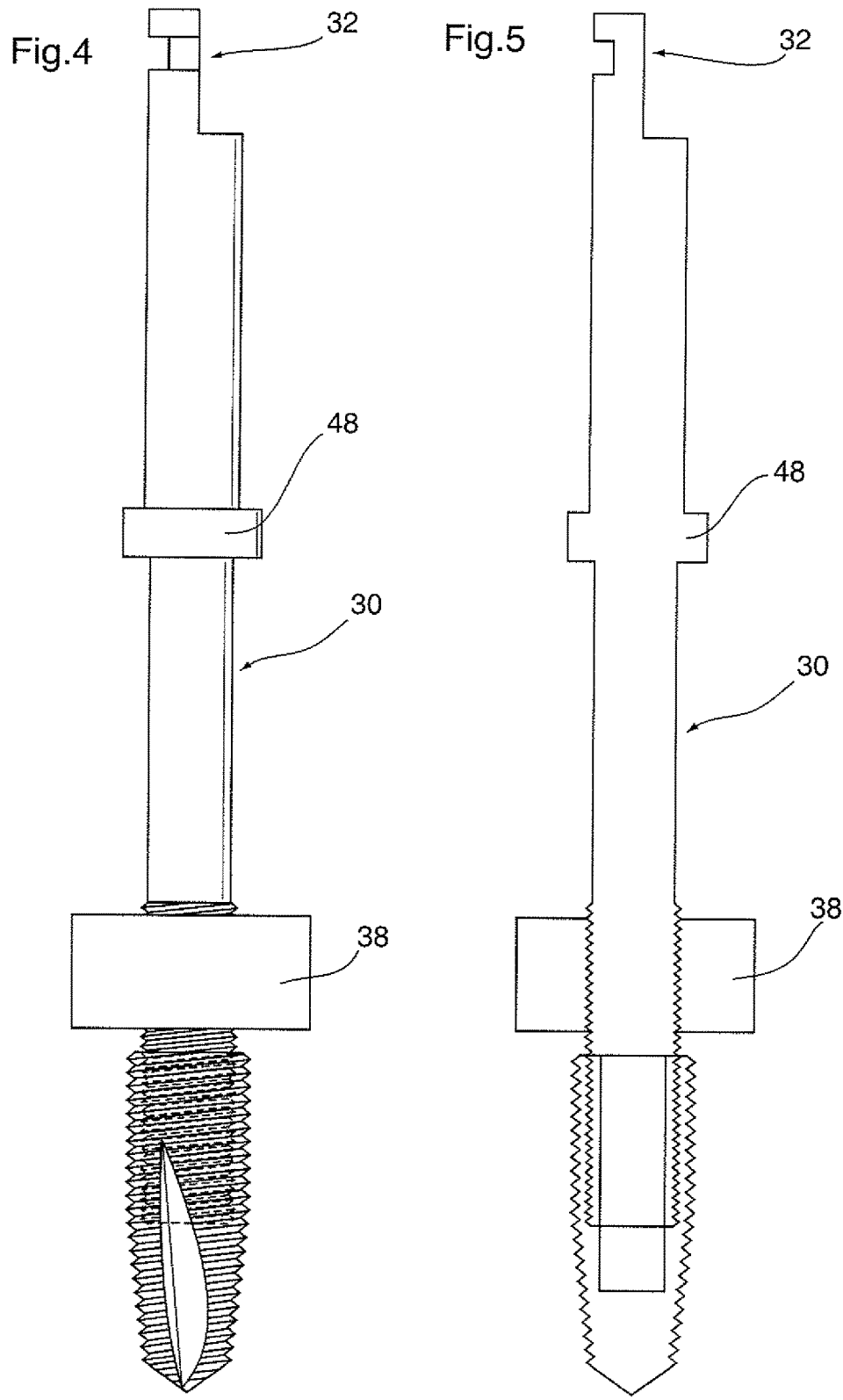

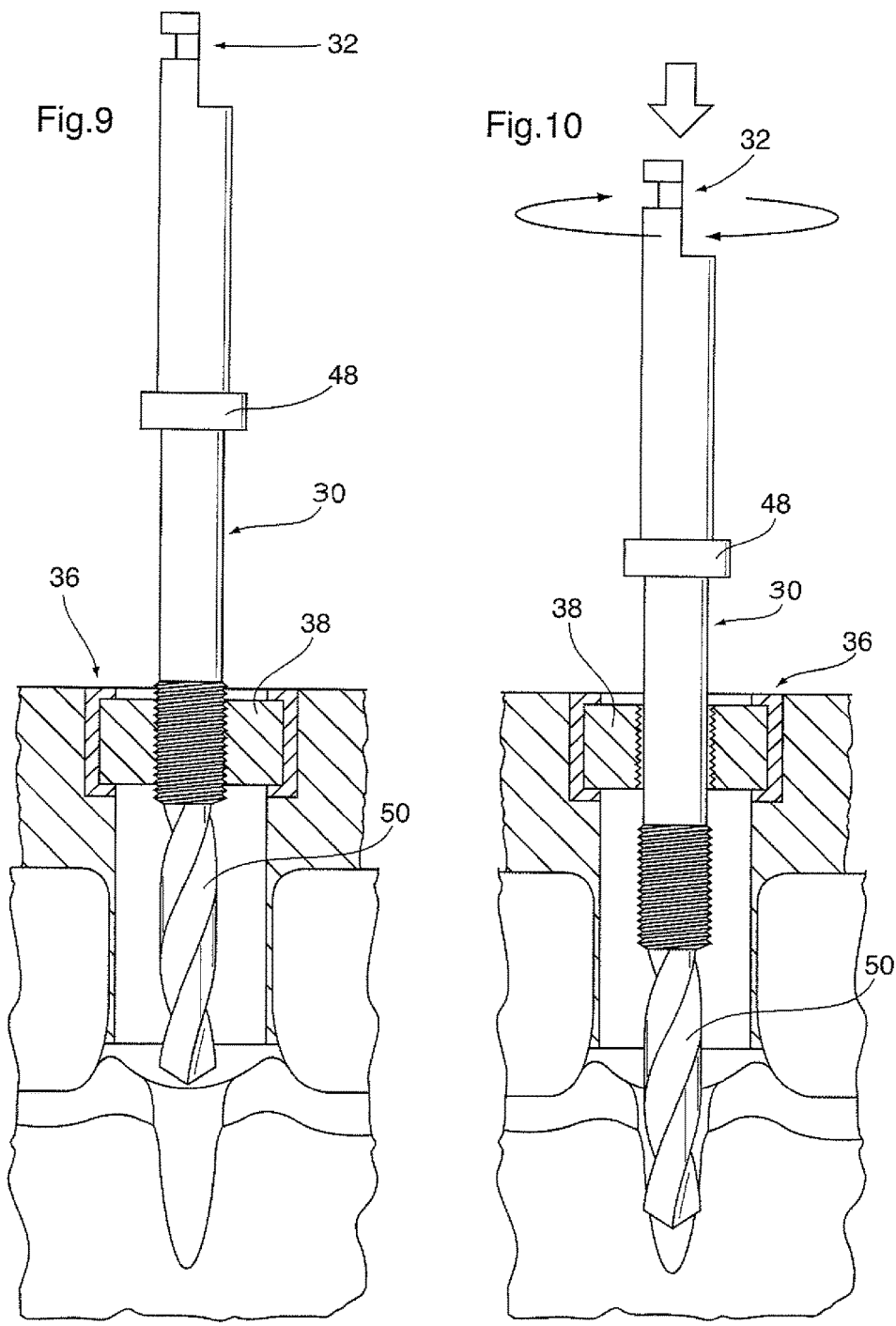

DENTAL IMPLANT POSITIONING SYSTEM

CROSS-REFERENCE TO RELATED APPLICATION

This application claims benefit from U.S. Provisional Application No. 61/707,121 filed Sep. 28, 2012 which is incorporated herein by reference in its entirety.

FIELD

This invention relates to the field of dentistry. In particular, the invention relates to the positioning of dental implants or drills, including self-drilling, self-tapping dental implants.

INTRODUCTION

The procedure required to place a dental implant in a patient's jawbone typically involved the use of as many as five drills followed by a tap, all of which must be operated at relatively low speed. In addition, up to five guide pins may be used to assess angulation throughout the drilling procedure. This means that the surgical procedure itself involves a plurality of steps, all of which are conducted at relatively slow speeds, which thus prolong the surgical procedure and decrease precision. In addition, the procedure involved the use of many components including the set of drills, guide pins and tap.

The self-drilling, self-tapping dental implant was designed to simplify and shorten the extended surgical procedure required to place a dental implant in the host bone by replacing all the steps mentioned above. See U.S. Pat. No. 7,008,227, the entire contents of which are incorporated herein by reference.

The self-drilling, self-tapping implant comprises a body and a head. The body includes a lead thread, an intermediate thread and a distal thread. The implant further includes a central bore within the head. There is a thread within the bore for receiving a dental prosthesis. The tip includes two cutting edges and two flutes that terminate at the end of the intermediate portion.

In order to install the self-drilling, self-tapping implant, the head of the implant may be gripped by means of a dental tool. Force is then applied in the direction of the bone and the tool is used to rotate the implant. The cutting edges then begin to remove bone chips which are forced to flow along the flutes. The implant advances into bane as the threads engage the bone, and continues until the implant has been installed to the desired depth. When the implant has been positioned to the desired depth, the tool is removed from the head portion of the implant.

Installation of the self-drilling, self-tapping dental implant may be accomplished free-hand by the dentist, or with the guidance of a surgical template. Typically, when an implant is to be installed with the aid of a surgical template, a dentist prepares a cast of the patient's dental arch. That cast is forwarded to a dental laboratory for creation of a suitable template. When the laboratory technician and the dentist have determined the appropriate location of the implant given the conditions of the patient's dental arch, the laboratory constructs a suitable template with a bore defining the desired long axis of the implant, and forwards it to the dentist. The dentist, guided by the bore in the template, installs the implant.

One of the problems that can arise in this situation is that the template provides only a rough or imprecise guide as to where the dentist should place the implant. Practically speaking, the dentist is allowed considerable leeway in selecting the final position of the implant when using a template. Thus, because the dentist is given some leeway in deciding where the implant is to be placed, the location of the implant is not controlled and may not reflect the position intended. The error in location may be in several directions. Accordingly, the implant may injure a vital structure such as the inferior alveolar neurovascular bundle, adjacent tooth roots, the maxillary sinus or the floor of the nose. Moreover, the design of the prosthesis may be non-ideal in terms of strength, esthetic appearance or the biological response it provokes.

When three-dimensional (3D) visualization is combined with 3D virtual surgery, the pre-surgical planning is improved. When planning in 3D, digital models are rendered from cone-beam computed tomography (CT) scans of the patient that are used to provide precise, comprehensive information which enables faster and more accurate surgery. Cone-beam CT scanners are specialized for scans of the head and face region and can focus on a very specific area.

Implant planning software programs are available such as coDiagnostiX (http://www.straumann-cares-digital-solutions.com/com-index/digital-solut-ions/guided-surgery.htm) (Straumann A G, Basel, Switzerland) or Simplant (http://www.materialise.com/materialise/view/en/2970306-SimPlant.html) (Materialise Dental, Leuven, Belgium).

It would be advantageous to provide a system to allow a self-drilling, self-tapping dental implant to be used in a guided fashion together with or without implant planning software such as coDiagnostiX and surgical template fabrication techniques utilizing instrumentation such as gonyX.

SUMMARY

According to the present invention there is provided a system for use in installing a dental implant in a jawbone of a patient. The system includes a threaded drive shaft rotatable about an axis and guide means for supporting the drive shaft with its axis oriented in a path along which the implant is to be installed. The guide means has a threaded bore for receiving a drive shaft and an opening which extends parallel to the axis of the drive shaft and opens radially outwardly from the bore. The drive shaft can then be engaged with and disengaged from the guide means by radial displacement of the shaft parallel to its axis. A drill is coupled to a leading end portion of the drive shaft. The drill may be a self-drilling/self-tapping implant or a twist drill bit, in which case the bit may be integral with the drive shaft, forming a "guided drill". Means is provided for rotating the drive shaft in a direction to cause the drill to penetrate the jawbone of the patient.

An important feature of the system provided by the invention is that the drive shaft can be engaged with and disengaged from the guide means by radial displacement of the drive shaft. This minimizes the extent to which the patient is required to open his or her mouth in order to accommodate the instruments that are being used to install the implant. Visualize a drive shaft of several centimeters in length plus an implant on the leading end of the drive shaft. If the drive shaft and implant could be moved only in the axial direction, the patient's mouth would have to be opened to accommodate the full overall length of the drive shaft and implant. To the contrary, the system provided by the invention allows the drive shaft and guide body to be "rolled around" the exterior of the patient's teeth until the appropriate location is reached, and then engaged with the guide means by inward radial movement. Discomfort to the patient is thereby minimized.

In a preferred embodiment, the guide means comprises a C-shaped holder which provides an opening outwardly of the teeth of the patient in use and in which the guide body can be engaged. Preferably, the interior surface of the holder has a recess or guideway that receives the guide body when the drive shaft and implant are being fitted prior to installation. The guide body and recess or guideway are made to close tolerance limits so that the drive shaft is accurately located with minimum "play", which obviously makes for accuracy when the implant is installed.

The guide means is located in fixed relationship with respect to the intended location of the implant by means of a surgical template which is custom made to fit a patient's mouth in advance. The holder of the guide means may be embedded in the template.

The guided drill may have a lead drilling portion for drilling a bore in the bone, a proximal intermediate portion which is threaded, and a distal intermediate portion which is unthreaded, with the unthreaded portion being adapted to pass through the bore thread in the holder so that the drill may be rotated and advanced or retracted with respect to the guide. In accordance with one embodiment of the invention, the guided drill or drive shaft includes a stop for limiting axial advance of the drill relative to the guide.

The components of the system may be part of a kit that includes a guided drill for drilling a bore in dense bone to accommodate the self-drilling, self-tapping implant (or any other kind of implant if so desired) and a dental drill head. The guided drill advantageously comprises a lead twist drill portion for drilling into bone. The guided drill further includes a proximal intermediate threaded portion, a distal intermediate unthreaded portion of comparatively narrower diameter, a stop and a distal portion with a latch terminus. The latch terminus may be of any suitable configuration which may be provided to facilitate engagement with a drill head.

In accordance with another feature of the invention, the thread of the proximal intermediate portion of the guided drill, the proximal portion of the drive shaft, the thread of the bore of the guide and the external thread of the implant all have the same axial pitch.

The lead 2 or 3 threads of the proximal intermediate portion of the guided drill or the proximal portion of the drive shaft and/or the distal 2 or 3 threads of the guide may advantageously be tapered to assist in preventing binding and stripping of the threads.

The pitch of the external thread of the implant, the proximal portion of the drive shaft and the threaded bore of the guide may be all the same, so that as the implant is rotated, its thread will advance along a helical groove being simultaneously cut into the bone, at the same feed rate as the drive shaft travels through the guide. The pitch of the proximal intermediated threaded portion of the guided drill, the proximal portion of the drive shaft and the threaded bore of the guide are all the same, so that the guide may be used interchangeably with the guided drill and the drive shaft.

The kit may include a variety of implant lengths with corresponding drive shafts and guided drills. The use of guided drills and milling cutters (not illustrated) may be used to allow an implant to be installed in a drilled osteotomy in sites where the bone is very hard. Guided drills may comprise a lead portion for drilling bone equal in length to the length of the selected implant. The distance between the stop and the distal surface of the wedge-shaped guide is equal to the desired length of implant installation.

DRAWINGS

In order that the invention may be more clearly understood, reference will now be made to the accompanying drawings which illustrate a particular preferred embodiment of the invention by way of example, and in which:

FIG. 3 is an exploded detail view showing the relationship between the holder and the drive shaft of the system;

FIGS. 4 and 5 are elevational and sectional views respectively of the drive shaft and implant in a location prior to installation of the implant;

FIGS. 9 and 10 are views similar to FIGS. 4 and 8 showing the system in use in the situation in which pre-drilling of the patient's jawbone is necessary;

DESCRIPTION OF VARIOUS EMBODIMENTS

Figure 1:
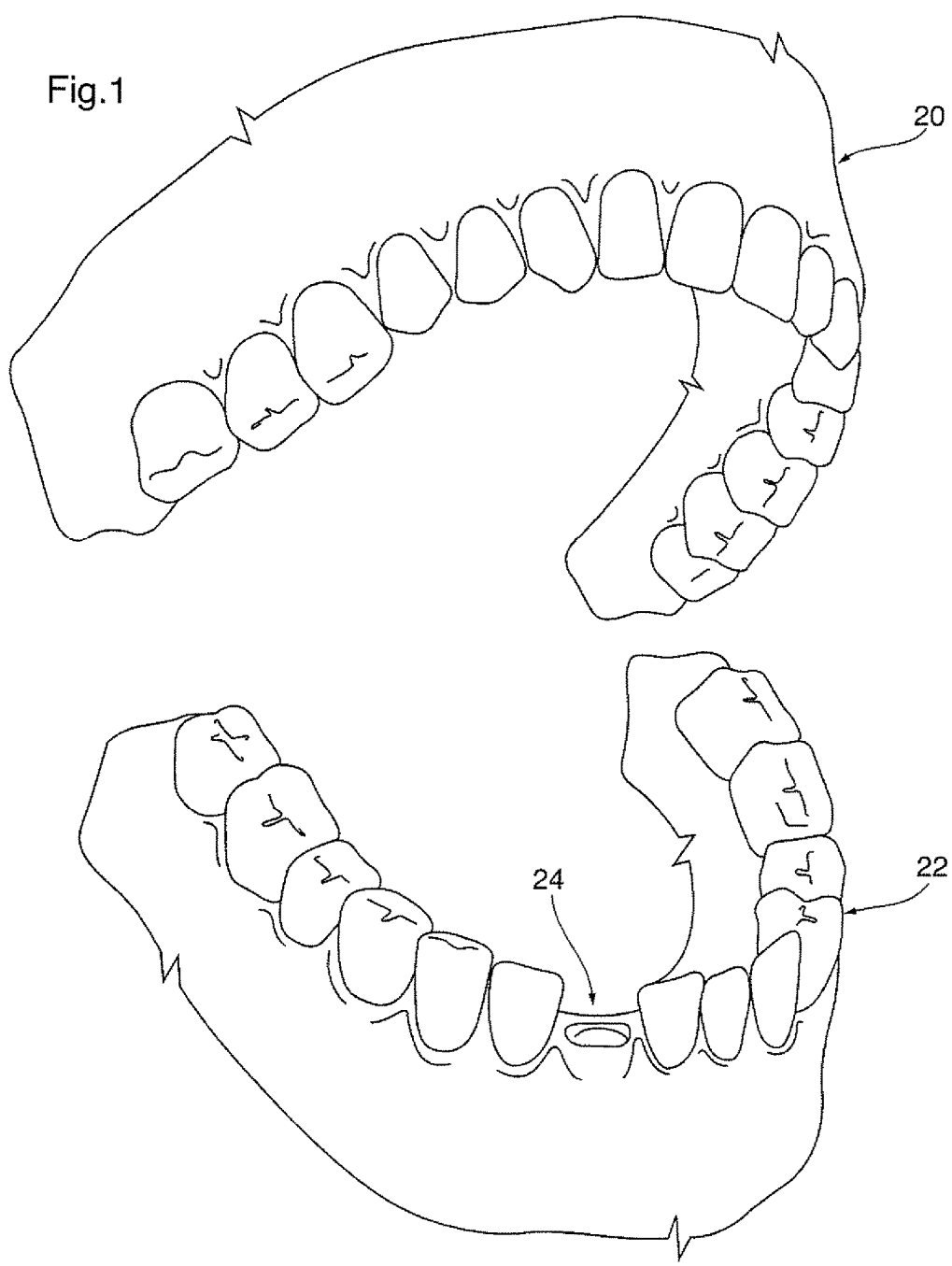
FIG. 1 is a schematic illustration of the jaws of a patient preparatory to installation of a dental implant.

Referring first to FIG. 1, upper and lower jaws 20 and 22 respectively of a patient are shown in an open condition as for installation of a dental implant. The intended location of the implant is indicated at 24.

Figure 2:
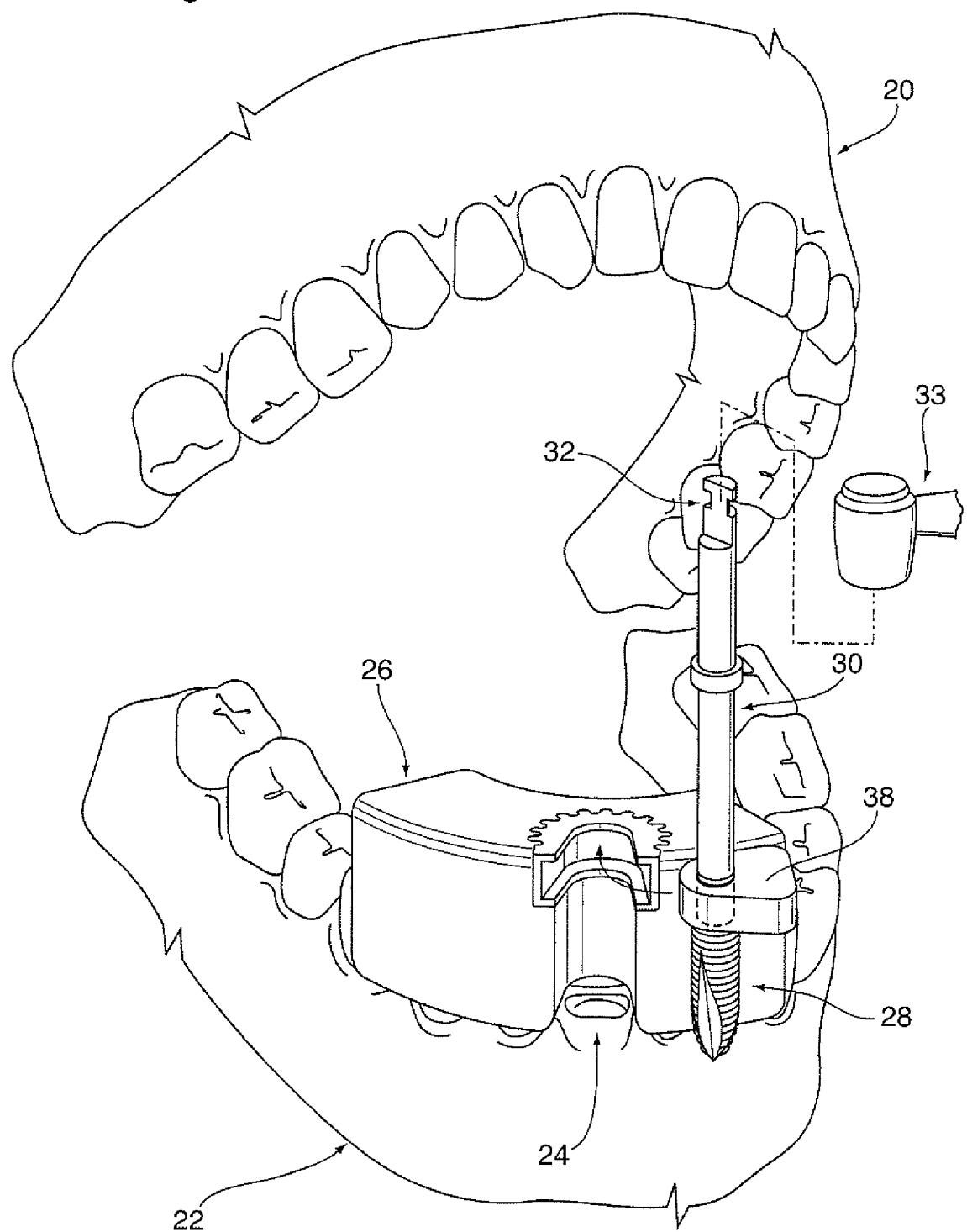
FIG. 2 is a view similar to FIG. 1 showing the system of the invention in place on the lower jaw of the patient.

FIG. 2 shows components of the system of the invention in place on the lower jaw 22.

A surgical template is illustrated diagrammatically at 26. The template will be made by technicians in a dental laboratory prior to commencement of the implant installation procedure. The template will have been molded closely to a cast of the patient's jaw at the location at which the implant is to be installed.

The implant itself is shown at 28 and is a self-drilling, self-tapping dental implant, for example of the type shown in U.S. Pat. No. 7,008,227 supra. The implant is threaded onto the leading lower end of a drive shaft 30. Alternative connection means such as a Torx drive socket may be used to attach the implant to the drive shaft. Drive shaft 30 extends about an axis A-A and in a path in which the implant is to be installed, namely vertically in the illustrated embodiment. The upper end of the drive shaft is provided with a latch component 32 by which a dental drill head 33 can be coupled to the drive shaft for rotating the shaft. As is described in the '227 patent supra, the implant is designed to drill into the jawbone of the patient in response to rotation of the drive shaft, typically in the clockwise direction.

FIG. 3 shows a leading lower end portion 34 of the drive shaft 30 that threads into the upper end of the implant so that the implant is driven in rotation when the drive shaft is rotated. Clockwise rotation will drive the implant to drill into the jawbone, while counter clockwise rotation after installation will leave the implant in the jawbone and withdraw the drive shaft 30.

As discussed previously, the system includes guide means located in a fixed relationship with respect to the location (24) at which the implant is to be installed. As best seen in FIG. 2, the guide means includes a holder 36 that is embedded in the surgical template 26 and a guide body 38 that is threaded to the drive shaft 30. Holder 36 is generally C-shaped in plan and opens radially outwardly, i.e. in the direction towards the exterior of the teeth of the patient. A recess or guideway 40 is formed in the inner surface of the holder 36 and receives the guide body 38 when the drive shaft and implant are in position to install the implant. The recess 40 in the holder 36 has a shape that tapers inwardly from the open outer end 42 of the holder and the guide body 38 has a complimentary shape. The co-operating surfaces of the holder and guide body are made to close tolerances so that the drive shaft is coupled to the holder and hence to the surgical implant of the jaw of the patient with minimum freedom of lateral movement. In other words, the drive shaft is held relatively immobile laterally with respect to the site at which the surgery is to be performed, which makes for maximum accuracy.

The design of the guide means is such that the drive shaft 30 can be fitted to and released from the holder 36 by radial displacement of the drive shaft. This means that the drive shaft can be installed by in effect "rolling" the drive shaft around the exterior of the patient's teeth, while maintaining the drive shaft substantially vertical (in the described embodiment) and without requiring the patient to open his or her jaws beyond a comfortable amount. This contrasts with the situation which would arise if the full overall length of the drive shaft and implant had to be accommodated above the upper surface of the surgical template 26.

Figure 6:
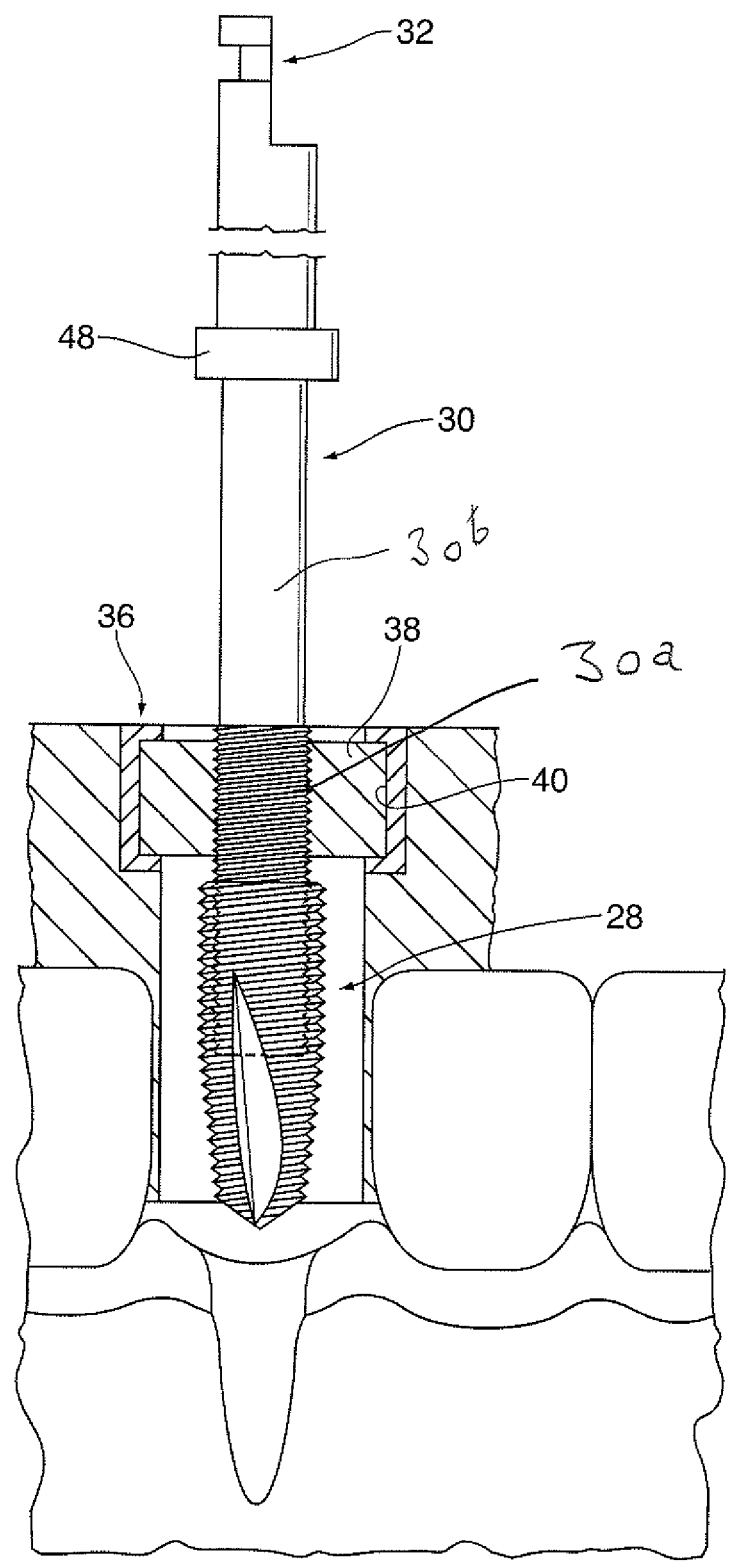
FIG. 6 is a view similar to FIG. 4 showing the drive shaft and implant in place prior to installation.

FIGS. 4, 5 and 6 show the drive shaft in an uppermost position preparatory to beginning installation of the implant. In FIG. 6, part of the surgical template 26 is also shown, as is the guide body 38, which is received within the recess 40 of guide holder 36. The implant 28 is shown in FIG. 6 poised to move downwardly through the gum of the patient and into the jawbone. Normal surgical procedures will, of course, be taken, possibly including procedures to expose the bone itself.

Figure 7:
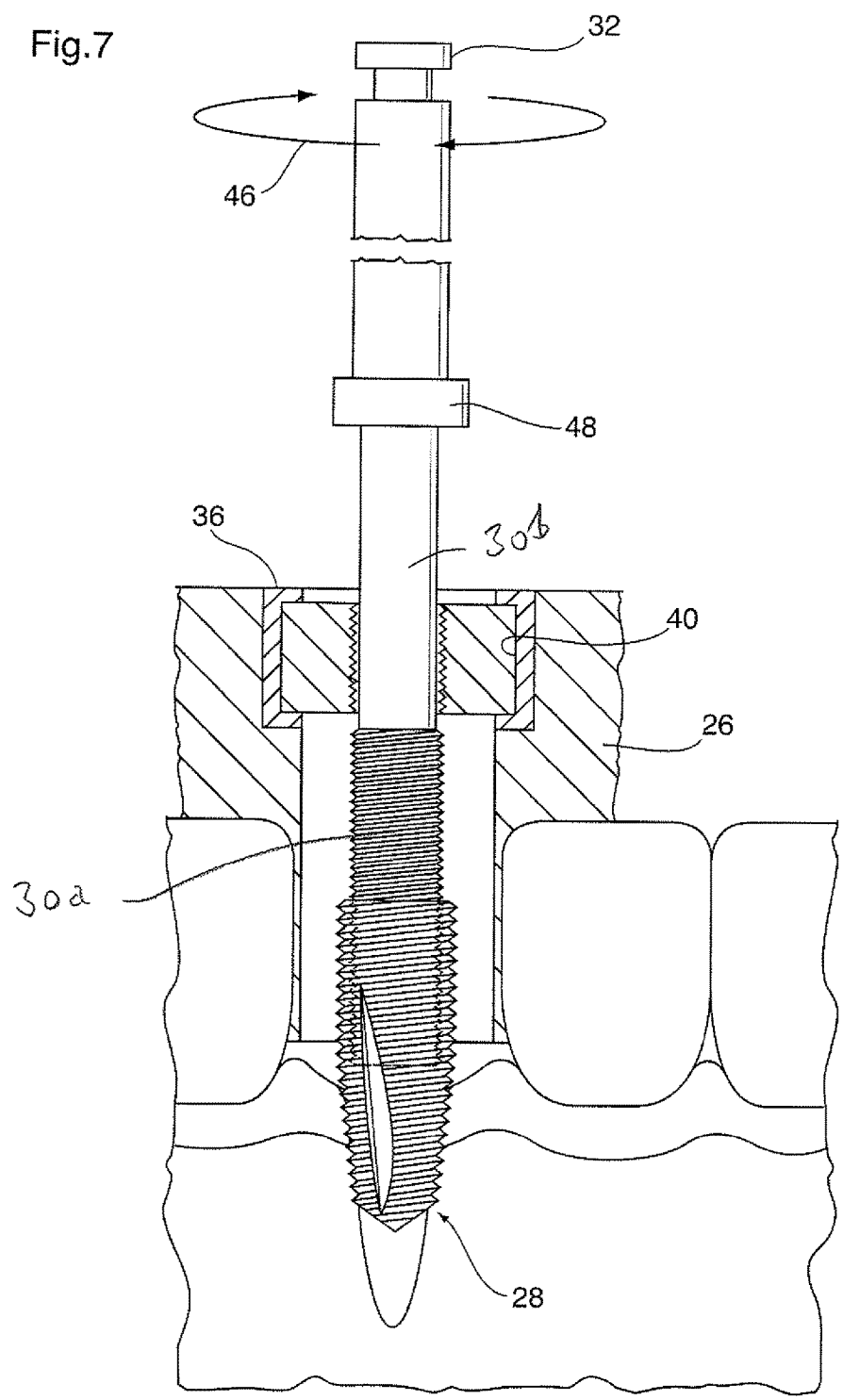
FIG. 7 is a view similar to FIG. 6 showing the implant in the course of installation.

FIG. 7 shows the implant drilling into the jawbone in response to rotation of the drive shaft as indicated by the arrows 46.

Figure 8:
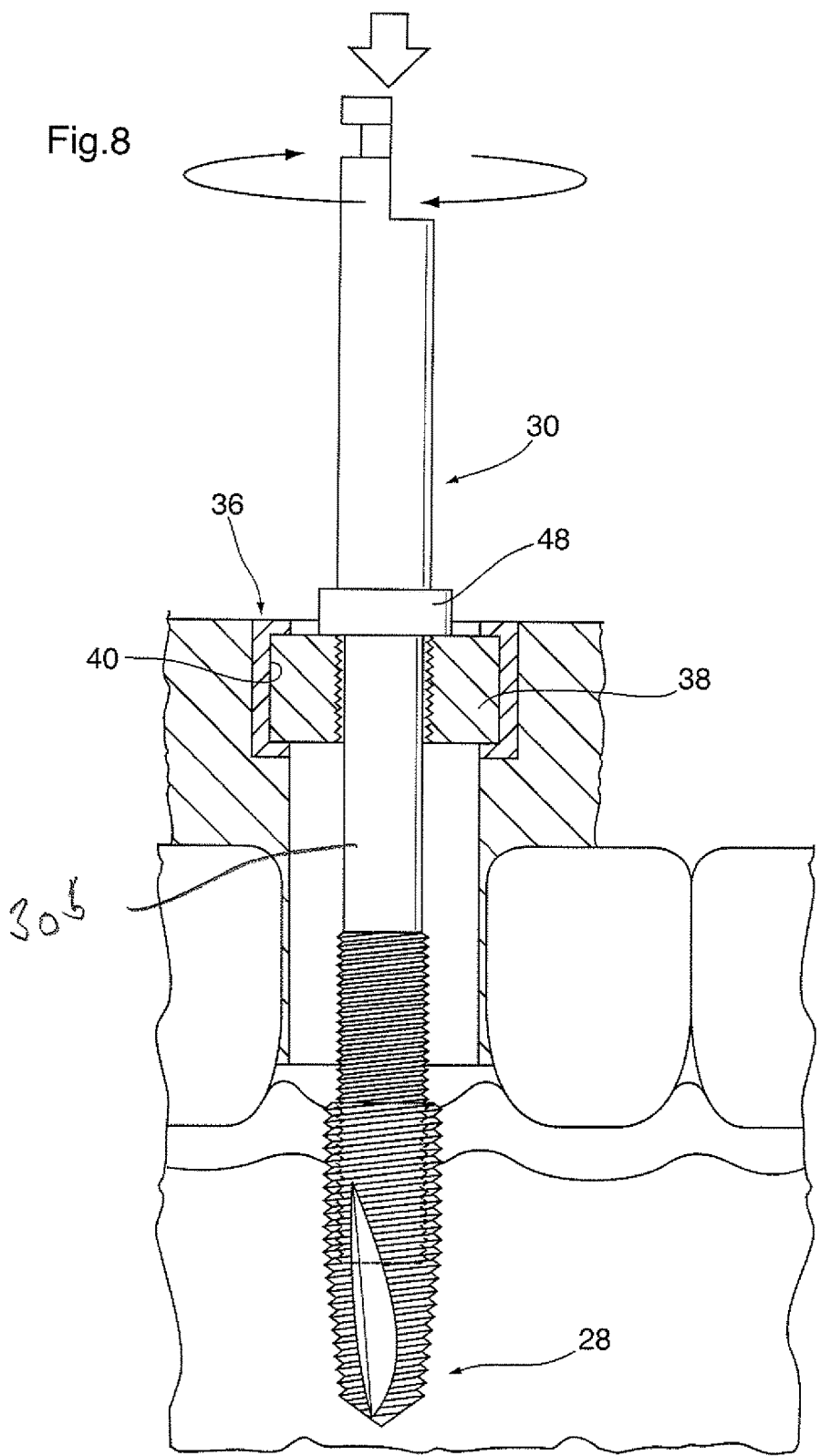
FIG. 8 is another similar view showing the implant fully installed.

A stop 48 is provided at the top end of the drive shaft 30 and is shown in FIG. 8 in contact with the upper surface of the guide body, defining the maximum penetration position for the implant.

While it is possible that the drive shaft 30 could be threaded over its entire length, it has been found preferable to thread only a lower portion of the drive shaft so that, as the drive shaft advances it advances the tip of the implant into the bone. During this initial period of advance of the implant into bone, before full engagement of the leading threads of the implant with the bone, unless downward force is applied by the surgeon to the dental hand piece sufficient to cause the tip of the implant to penetrate the bone to the extent that its first 2 to 4 threads engage the bone fully and cause it to self-advance through the bone, push-back will cause the surgical template to lift off the teeth, and the implant will spin in the bone. A very secure surgical template will resist this push-back, and in fact the inter-engagement of the threaded proximal portion of the drive shaft with the threaded bore of the guide will provide the downward impetus to drive the implant into the bone deeply enough for it to become self-advancing. Bone being what it is, that is heterogeneous in density, once the implant begins to self-advance, there will be no assurance that it will advance at precisely the same feed rate as it would if it were being driven by a driver threaded along the entire length of the shaft. It will never advance more quickly, but may advance more slowly, than the advance of the driver. This discrepancy in feed rates will cause undesirable push-back and lift off of the surgical template.

Moreover, self-advancing of the implant through bone of heterogeneous density may cause it to deviate very slightly from the desired pathway of insertion thus exceeding the close tolerance limits of the threaded proximal portion of the drive shaft in the threaded bore of the guide. Therefore, it would be advantageous for the drive shaft to decouple from the threads of the guide once the desired result of engaging the lead threads of the implant in bone has been achieved so that some "play" could occur so as to not dislodge the surgical template either by vertical force caused by discrepancies in feed rate or by lateral forces caused by a deviation in the path of insertion. The dental surgeon can then manually determine the speed of rotation of the drive shaft, e.g. increase the speed to increase the speed at which the implant drills into the jawbone.

As noted previously, the guided drill may have a lead drilling portion for drilling a bore in the bone, a proximal intermediate portion which is threaded, and a distal intermediate portion which is unthreaded, with the unthreaded portion being adapted to pass through the bore thread in the holder so that the drill may be rotated and advanced or retracted with respect to the guide.

FIG. 6 for example shows a lead drilling portion (the implant 28), a proximal intermediate portion (the threaded portion 30a) and a distal intermediate portion (30b) which is unthreaded down to the level of top surface of the guide means. FIG. 7 shows the drive shaft having moved down to the position at which it comes free from the guide body 38, so that the surgeon is able to determine the rotational speed of the drive shaft. FIG. 8 shows the implant fully installed and that the stop 48 prevents further downward movement of the drive shaft.

In a situation in which the system of the invention is being used to install a self-drilling and self-tapping implant, the implant itself will advance downwardly into the bone simply by virtue of the cutting action that derives from the design of the implant. Once the lead 2 to 4 threads of the implant engage the bone there is no need for downward pressure to cause the implant to advance.

FIGS. 9 and 10 are views similar to FIGS. 7 and 8 respectively and illustrate use of the system of the invention for pre-drilling the jawbone of the patient with a dental twist drill 50 or a milling cutter, i.e. where the implant is not self-drilling. In this application of the invention, it is important that the surgeon be able to exert downward pressure on the drive shaft in order to cause the drill to advance.

Figure 11:
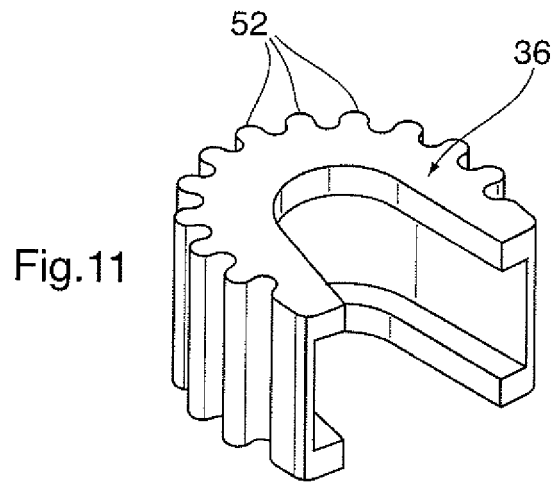
FIG. 11 is a perspective view of the holder of the guide means of the system in insolation; and, FIG. 12 is a detail sectional view showing the implant installed.

Finally, as indicated previously, FIG. 11 shows the holder 36 of the guide means in isolation. The external surface of the holder is provided with a series of vertical ribs 52 or other means of retention, which are useful in ensuring that the holder is firmly embedded in the surgical template.

Figure 12:
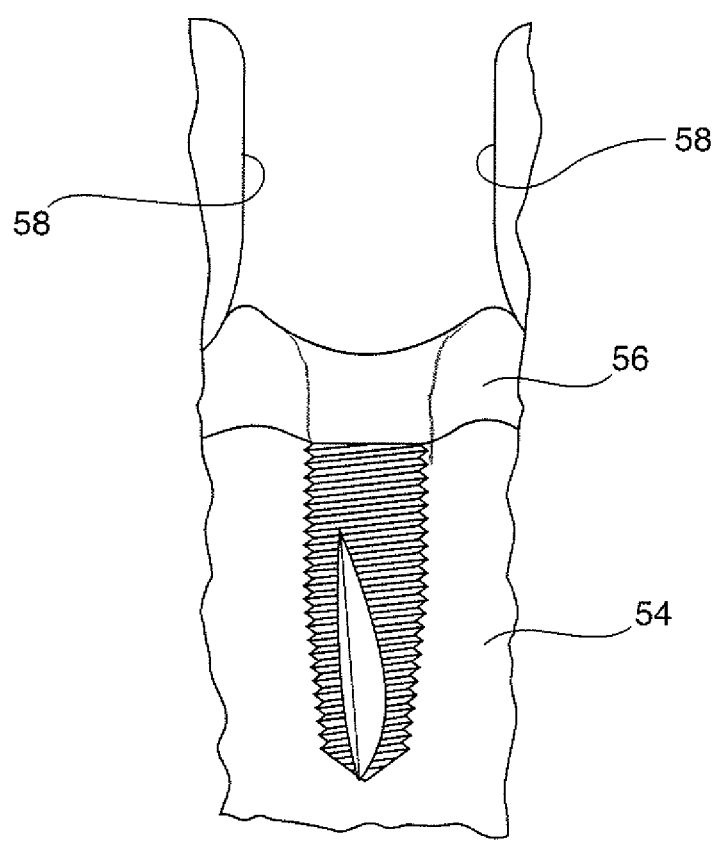

FIG. 12 shows the implant fully installed in the jawbone 54 of the patient below the gum 56, and portions of adjacent teeth 58.

It will of course be appreciated that the preceding description relates to a preferred embodiment of the invention, and that modifications are possible and will be evident to a person skilled in the art. For example, in other embodiments, it might be possible to provide partial threads within a recess in the surgical template that would take the place of the holder 36 and associated recess. The drive shaft could then be accommodated directly in the surgical template without the need for an intermediate guide body 38.

The invention claimed is:

1. A system for installing a dental implant in a jawbone of a patient, the system comprising:
    a threaded drive shaft rotatable about an axis, the drive shaft having a lower threaded portion and an upper unthreaded portion;
    guide means for supporting the drive shaft with the axis of the drive shaft oriented in a path along which the implant is to be installed, the guide means having a C-shaped holder defining an opening into which a guide body is inserted, the guide body including a threaded bore for receiving the drive shaft such that the drive shaft advances through the guide body by first threading the lower threaded portion through the threaded bore of the guide body and then sliding the upper unthreaded portion through the threaded bore of the guide body, wherein the opening opens radially outwardly to enable the guide body and the drive shaft to be engaged with and disengaged from the C-shaped holder of the guide means by radial displacement of the guide body and the drive shaft;
    a self-drilling, self-tapping implant having bone-engaging external threads and having internal threads coupled to the lower threaded portion of the drive shaft wherein the guide body is internally threaded with a thread pitch that matches a pitch of the external threads of the self-drilling, self-tapping implant and which also matches a pitch of the lower threaded portion of the drive shaft; and,
    a dental drill head for rotating the drive shaft in a direction to cause the self-drilling, self-tapping implant to penetrate the jawbone of the patient.

2. The system as claimed in claim 1, wherein the body and holder are complementarily shaped for precise location of said drive shaft in said bore and with respect to the location in a dental arch at which the self-drilling, self-tapping implant is to be installed.

3. The system as claimed in claim 2, wherein the holder has a shape that tapers inwardly from said opening, and the guide body is shaped to fit closely into the holder for stably locating the drive shaft with respect to the jawbone of the patient.

4. The system as claimed in claim 1, wherein the holder of the guide means is embedded in a surgical template formed to be fitted into the mouth of the patient, for locating the guide means in fixed relationship with respect to the location at which the self-drilling, self-tapping implant is to be installed.

5. The system as claimed in claim 1, wherein the drive shaft is provided with a stop for defining a position of maximum penetration of the implant by contact of the stop with an upper surface of the guide body.

6. A kit of parts for installing a dental implant in a jawbone of a patient, the kit comprising:
    a self-drilling, self-tapping implant having bone-engaging external threads and internal threads;
    a threaded drive shaft rotatable about an axis, the drive shaft having a lower threaded portion for engaging the internal threads of the implant and an upper unthreaded portion;
    guide means for supporting the drive shaft with the axis of the drive shaft oriented in a path along which the self-drilling, self-tapping implant is to be installed, the guide means having a C-shaped holder defining an opening into which a guide body is inserted, the guide body including a threaded bore for receiving the drive shaft such that the drive shaft advances through the guide body by first threading the lower threaded portion through the threaded bore of the guide body and then sliding the upper unthreaded portion through the threaded bore of the guide body, wherein the opening opens radially outwardly to enable the guide body and the drive shaft to be engaged with and disengaged from the C-shaped holder of the guide means by radial displacement of the guide body and the drive shaft;
    wherein a trailing end of the drive shaft is adapted to be releasably coupled to a dental drill head for rotating the drive shaft to cause the self-drilling, self-tapping implant to penetrate the jawbone of the patient; and
    wherein the guide means is internally threaded with a thread pitch that matches a pitch of the external threads of the self-drilling, self-tapping implant and which also matches a pitch of the lower threaded portion of the drive shaft.

7. A method of installing a dental implant in a jawbone of a patient, comprising the steps of:
    providing the kit of parts as claimed in claim 6;
    providing a surgical template molded to fit a dental arch of a patient at the location at which the self-drilling, self-tapping implant is to be installed, the template having a holder embedded therein;
    engaging a guide body of the guide means with the holder via said opening;
    engaging the threaded drive shaft with the threaded bore in the body; and,
    rotating the drive shaft in a direction to cause the self-drilling, self-tapping implant to penetrate the jawbone of the patient.

* * * * *